(12) United States Patent
Barlet et al.

(10) Patent No.: US 10,370,634 B2
(45) Date of Patent: Aug. 6, 2019

(54) INCUBATION AND DETECTION DEVICE

(71) Applicant: ADVENCIS, Mutzig (FR)

(72) Inventors: Pierre Barlet, Strasbourg (FR);
Guillaume Sala, Strasbourg (FR);
Joseph Pierquin, Molsheim (FR)

(73) Assignee: ADVENCIS, Mutzig (FR)

(*) Notice: Subject to any disclaimer, the term of this patent is extended or adjusted under 35 U.S.C. 154(b) by 111 days.

(21) Appl. No.: 15/302,921

(22) PCT Filed: Apr. 7, 2015

(86) PCT No.: PCT/FR2015/050904
§ 371 (c)(1),
(2) Date: Oct. 7, 2016

(87) PCT Pub. No.: WO2015/155468
PCT Pub. Date: Oct. 15, 2015

(65) Prior Publication Data
US 2017/0037355 A1    Feb. 9, 2017

(30) Foreign Application Priority Data

Apr. 7, 2014 (FR) .................................. 14 53047
Aug. 28, 2014 (FR) .................................. 14 58040

(51) Int. Cl.
C12M 1/34    (2006.01)
C12M 1/12    (2006.01)

(52) U.S. Cl.
CPC ............ C12M 41/36 (2013.01); C12M 23/04 (2013.01); C12M 41/12 (2013.01)

(58) Field of Classification Search
CPC .................................................... C12M 41/36
See application file for complete search history.

(56) References Cited

U.S. PATENT DOCUMENTS

| 3,630,849 A * | 12/1971 | Land ..................... C12M 23/10 |
| | | 435/305.4 |
| 4,301,252 A * | 11/1981 | Baker .................... C12M 23/48 |
| | | 119/319 |
| 2003/0155528 A1 | 8/2003 | Tokuda |
| 2005/0051723 A1 * | 3/2005 | Neagle ................... C12M 41/14 |
| | | 250/306 |

FOREIGN PATENT DOCUMENTS

| GB | 2494202 A | 3/2013 |
| JP | 2010161978 A | 7/2010 |
| WO | 03022999 A1 | 3/2003 |
| WO | 2013110734 A1 | 8/2013 |

OTHER PUBLICATIONS

Week 201056, Thomson Scientific, London, GB; AN 2010-J89042.

* cited by examiner

*Primary Examiner* — Jonathan M Hurst
(74) *Attorney, Agent, or Firm* — Craft Chu PLLC; Andrew W. Chu

(57) ABSTRACT

The incubation and detection device includes a heater, a detection surface with at least one receptacle including a growth medium, and a detection system. There is also a system for preventing the formation of condensation in the receptacle, which includes a temperature-control formed by temperature sensors, heaters, coolers, and management device capable of collecting and analyzing the information collected by the sensor and controlling the heater and cooler so as to generate the desired incubation temperature and permanently apply a temperature gradient to the surface of the receptacle.

7 Claims, 2 Drawing Sheets

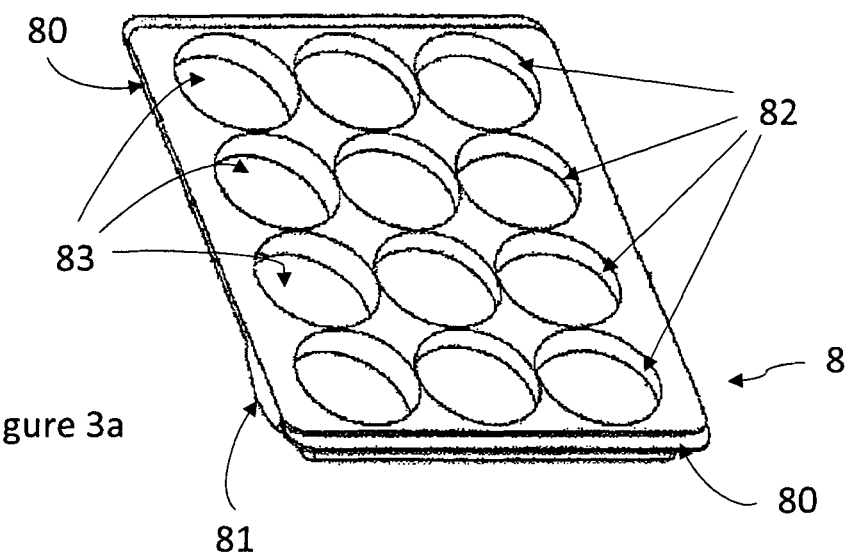
Figure 3a
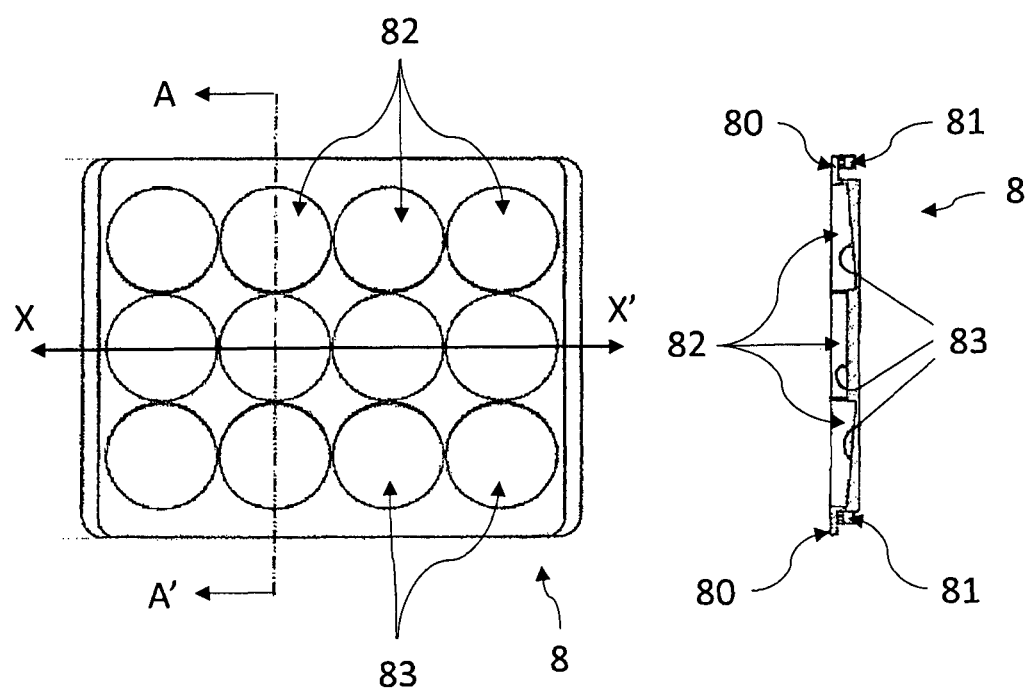
Figure 3b
Figure 3c

INCUBATION AND DETECTION DEVICE

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to the field of the detection of microorganisms in the growth phase.

The present invention will find its application primarily in the areas of the industrial and clinical microbiology, for example in the pharmaceutical, biotechnological, agro-food industries or also in the hospitals or medical analysis laboratories.

The invention relates more particularly to a device permitting an incubation and quick detection of the forming of colonies, from microorganisms present in a sample, at the surface of a membrane or a solid or semi-solid culture medium.

2. Description of Related Art Including Information Disclosed Under 37 CFR 1.97 and 37 CFR 1.98

Many techniques are presently implemented to permit the detection of contaminants, for example bacteria, in a sample to be tested.

The most conventional and oldest method consists of a deposition on the surface of an agar growth medium, whereby the latter may be more or less selective for one or several types of microorganisms.

The medium is then incubated at the appropriate temperature for the growth of the micro-organism(s) looked for, for a period that can be of up to several days.

Such a method has the drawback of requiring a relatively long incubation period in order to permit a detection with the naked eye of the colonies that were formed on the culture medium.

It is also known from the prior art to perform a polymerization chain reaction, also referred to as PCR, in order to determine the presence of specific microorganisms within a sample, by amplifying a DNA or RNA sequence.

These methods have the disadvantage of requiring several DNA strands, i.e. several contaminating microorganisms, generally at least several dozens of microorganisms. Such methods are therefore often less sensitive than the growth-based methods.

Also known is the possibility of using techniques consisting in marking the microorganisms so as to emphasize the contrast between the light emitted by the microorganisms and that emitted by the growth medium. The use of fluorescent viability markers such as CFDA (carboxyfluorescein diacetate) or non-fluorescent viability markers such as the TTC (tetrazolium chloride), or also of enzymes permitting to reveal the bioluminescence emitted for example by the ATP (adenosine triphosphate), permit an early detection of microorganisms, thanks to the use of optical systems sensitive to the characteristics of the emitted light, for example the wavelength or intensity.

Thus known is namely the United States patent application US 2003/0155528 that describes a method for detecting microorganisms, in which the latter are marked by suitable fluorescent reagents (such as fluorescein) permitting, on the one hand, to determine the amount microorganisms and, on the other, to judge whether they are viable or dead cells.

However, these techniques can prove cumbersome to be implemented and require the use of often expensive reagents and the presence of skilled labor forces. Moreover, they are not very suitable for detecting contaminants on a large number of samples, the marking operation being often difficult to be automated. In addition, these techniques have a risk of contamination of the sample. Indeed, the addition of reagents requires contacting said reagent with the microorganisms to be detected and is generally performed by opening the box containing the agar medium. Finally, contacting the reagent with the microorganisms has the risk of destructing the living cells forming a colony, especially when they are in early stages of growth (typically less than 100 cells).

From the prior art are also known methods based on a use of the light properties emitted naturally by microorganisms, for example by detecting the auto-fluorescence of said microorganisms. Thus, it is possible to facilitate the distinction of colonies using the contrast existing between the natural fluorescence emitted by said microorganisms and the non-fluorescent medium, on which they have been deposited.

A method using this principle is namely described in the international patent application WO 03/022999, in which certain optical properties of the colonies, such as auto-fluorescence, are used.

These techniques indeed permit to facilitate the detection of auto-fluorescent colonies or microorganisms, they then have a better contrast with the membrane or the culture medium. However, the level of naturally generated fluorescence is of a low magnitude, which does not permit to obtain fast detection times compared to a marking with a specific fluorophore, for example. In addition, the spurious emission of natural fluorescence by the culture medium or other particles present in the environment, such as dust, membrane fibers, or plastic particles from the medium, can cause a false positive result.

Finally, techniques using optical systems with high magnification can be used to visualize colonies in early stages of development: this is the case with microscopes, for example. However, these devices are limited to a detection on small surfaces, generally smaller than 1 mm2. Thus, the implementation of this type of techniques for the detection of one or more detection media, such as membranes or agar media, proves both long, of about several minutes per cm2, and expensive, due to the necessity of using scanning systems.

Also known from the prior art is patent WO 2013/110734, which provides a device for an early detection, and which can be automated, of the appearance of colonies on the surface of a growth medium, namely a membrane or an agar culture medium.

More particularly, in this device can be found a detection surface, on which rests a growth medium, for example a membrane or an agar medium, and a detection system, such as a linear scanner. This system includes at least one CCD sensor associated with an optical system.

This device is particularly interesting, because it namely permits to omit the use of expensive optical equipment or reagents. In addition, such a device permits to avoid any contamination by other microorganisms or particles, because the samples do not need to be moved during incubation, since the detection system is mobile.

However, it has been found that such a detection device, though very performant per se, could be further improved in its performance. It was also found that the developments made to such a detection device could also improve the performances of the incubation and detection devices that do not use a linear scanner, for example.

BRIEF SUMMARY OF THE INVENTION

To this end, the present invention relates to a device for the incubation and quick detection without fluorescence measurement of colonies resulting from the multiplication of microorganisms present in a sample to be tested, comprising:
- a heating means,
- a detection surface, on which is stationary arranged at least one receptacle closed with a transparent cover, in which a microorganism growth medium in the form of colonies is placed, this medium being of the type membrane or agar,
- a detection system, comprising an optical system permitting to visualize said colonies.

Said device is characterized in that it includes in addition a system for preventing the formation of condensation in said receptacle, which comprises a means for regulating the temperature, comprised of:
- a first temperature sensor operating above said receptacle,
- a second temperature sensor operating below said receptacle,
- said heating means, which acts above said receptacle,
- a cooling means acting below said receptacle, and
- management means capable of collecting and analyzing the information collected by said sensor means, and of controlling said heating and cooling means so as to generate the desired incubation temperature, on the one hand, and to permanently apply a temperature gradient onto the surface of said receptacle, on the other hand.

Advantageously, but not limited to, the detection system is of the linear scanner type and mounted flat to scan all or part of said surface, comprising at least one CCD or CMOS sensor, which is associated with an optical system comprised of at least one lighting and at least one optics, such as a lens.

The presence of the system for preventing the formation of condensation is particularly advantageous.

It permits indeed to prevent condensation from forming on the portion of the transparent cover inside the receptacle when the latter is closed. During the incubation of the receptacles, water droplets are indeed likely to form on the surface of the cover inside the receptacle, located on the side of the growth medium, whereby the latter may consist of a membrane placed on an agar medium or of only an agar medium, for example.

Condensation can prove particularly problematic in the systems for detecting colonies. Indeed, it causes the cover of the receptacle to become opaque and thus prevents any detection of microbial growth.

In the prior art, the solution chosen to be able to read the result on the agar or on the membrane consists in opening the receptacle, by removing the cover on which the condensation droplets are located. However, such a solution cannot be considered adequate, because it is highly likely to result into contamination of the culture medium placed in the receptacle by germs in the environment. It is then possible to get a false positive result, which can prove particularly problematic, even dangerous, namely in a clinical application.

The detection device according to the present invention, as described above, permits to cope with this problem.

In addition, the present device is particularly advantageous, because it permits to combine the functions of incubation of the sample and of detection of microorganisms present in said sample.

Such a combination has many advantages.

In particular, the analyzed sample is constantly kept at the right temperature, since it does not leave the device, which facilitates the growth of the microorganisms.

Moreover, such a device permits to avoid the handling errors of the receptacle containing the growth medium, whereby such errors are always possible with a robotic arm of an automated prior-art device. As a result, the risks of contamination of the sample are reduced, even suppressed with the device according to the invention.

Finally, the device associating the incubation of a sample and the detection of microorganisms also helps to reduce the condensation on the cover of the receptacle.

In a particular embodiment, the management means permit to apply a temperature gradient of at least 0.10° C. between the inside and the outside of the receptacle.

Such a temperature gradient permits, in a particularly optimal way, to prevent the formation of condensation at the level of the receptacle.

It should be noted that preferably the temperature measurement is performed by means of a thermocouple.

The incubation and detection device according to the invention preferably includes means for adjusting the position of the receptacle or receptacles, and thus of the growth medium or media, relative to the optical system.

The incubation and detection device according to the invention also includes means for automatically correcting the distance between the optical system of the receptacle or receptacles, and thus of the growth medium or media.

Such an embodiment permits a constant and accurate positioning of the receptacle relative to the optical system of the detection system, which will facilitate the detection of the colonies that develop on the growth medium, namely by ensuring that it is in the same field depth area of the optical system.

On the other hand, said incubation and detection device includes means for correcting the orientation of the receptacles, and thus of the growth medium or media, relative to the axis of the optical system.

This feature constitutes a particularly clever way to cope with the phenomena of optical aberrations that are likely to lead to the formation of images that are distorted. Such phenomena are due to the structure of the scanner. As a result, the growth media appear oval and some areas of said media are then not visible. Therefore, the detection system may not detect some colonies and therefore there is, because of the phenomena of optical aberrations, a significant risk of a false negative result.

Now, like a false positive result, a false negative result can be dangerous, especially when a patient must be diagnosed in clinical microbiology or the sterility of products such as drugs must be ensured in industrial microbiology.

Thus and advantageously, in the incubation and detection device according to the invention, each of the receptacle or receptacles rests on the detection surface through wedging means capable of inclining said receptacle and of providing same with the most favorable orientation relative to the optical system, depending on the position occupied by the receptacle during the detecting operation.

In an advantageous embodiment, the detection surface consists of a drawer slidably mounted in said device, capable of passing from an open position for receiving the closed receptacle or receptacles, to a closed position, in which a scanning of said receptacle or receptacles and thus of the growth medium or media can be performed by the detection system, said media being arranged directly in said drawer.

Still more advantageously, the receptacle or receptacles are arranged in the drawer through a removable tray.

Said removable tray is advantageously provided on the periphery and on the lower side with shims designed capable, when the drawer is in the closed position, of cooperating with adjustable depth stops said device includes internally, so as to bring, through lifting, and holding said tray, and thus the receptacle or receptacles it carries, at the right distance from the optical system.

In this particular embodiment, where the tray can accommodate several receptacles, the detection surface, on which the receptacles are arranged, includes recesses specifically dedicated to these receptacles, the bottom of each of said recesses has a determined inclination relative to the general plane of the tray, depending on the positioning of these recesses on said tray, so as to obtain the desired correction relative to the optical system.

Such a feature permits to cope with the phenomena of optical aberrations in a particularly satisfactory manner.

Thus and preferably, the detection surface, on which at least one receptacle is arranged, is configured to provide each of the receptacles with an inclination relative to the optical system.

Finally and also advantageously, the optical system of the incubation and detection device according to the invention includes a calibration system, which consists of a removable element for the purposes of cleaning and/or replacement.

Indeed, the detection systems of the linear scanner type need, in order to detect and adjust the level of white when taking pictures, to take a picture on a white strip, referred to as calibration strip, integrated into the detection system.

In case this calibration strip is soiled, for example by dust, which would be deposited on it, this results into deteriorating the quality of the images taken by the scanner, which have vertical color lines, preventing or potentially delaying the detection of micro-colonies located on these lines.

A contemplated solution consists in dismantling the entire apparatus in order to clean the white calibration strip. However, this solution is not satisfactory, because it is particularly tedious and long to be carried out. Another solution simply consists in replacing the apparatus in its entirety, which is expensive and environmentally unfriendly.

The solution provided in the detection device according to the invention permits to solve the problem arisen.

BRIEF DESCRIPTION OF THE SEVERAL VIEWS OF THE DRAWINGS

Further features and advantages of the invention will become clear from the detailed description of non-restrictive embodiments of the invention, with reference to the attached figures.

FIG. 3a shows a perspective view of part of the same detection device.

FIG. 3b shows a plan view of the same part.

FIG. 3c shows a cross-sectional view along the axis AA' of FIG. 3b.

DETAILED DESCRIPTION OF THE INVENTION

Figure 1:
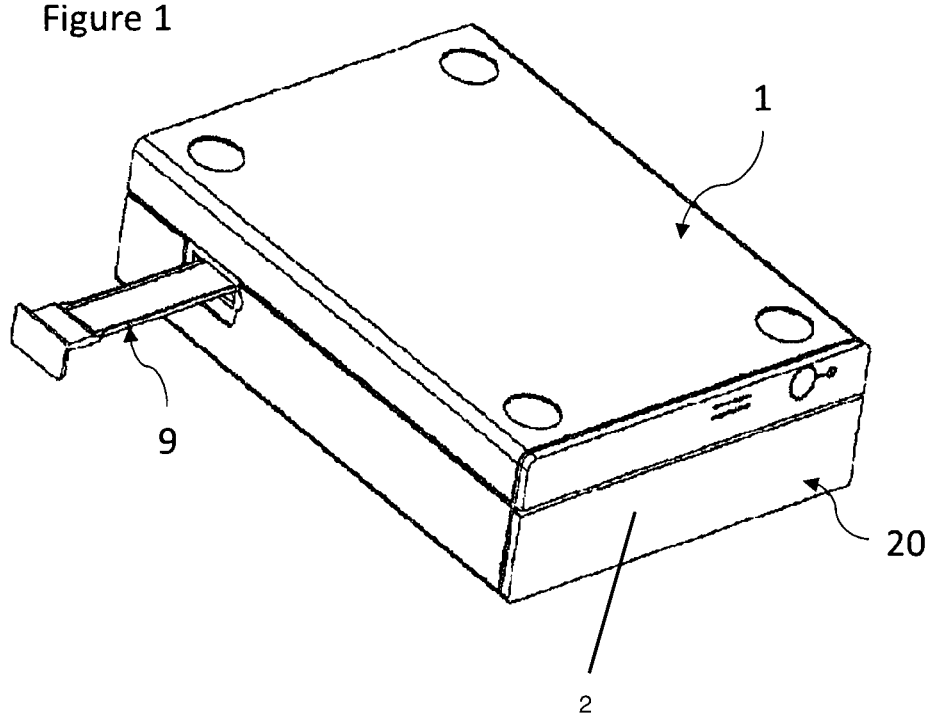
FIG. 1 schematically shows a perspective view of an incubation and detection device according to the invention.

When referring to FIG. 1, we can see a device for incubating and detecting microorganisms according to the invention. It is in the form of a box 1, provided with a drawer or tray 2, only the front 20 of which is visible.

Figure 2:
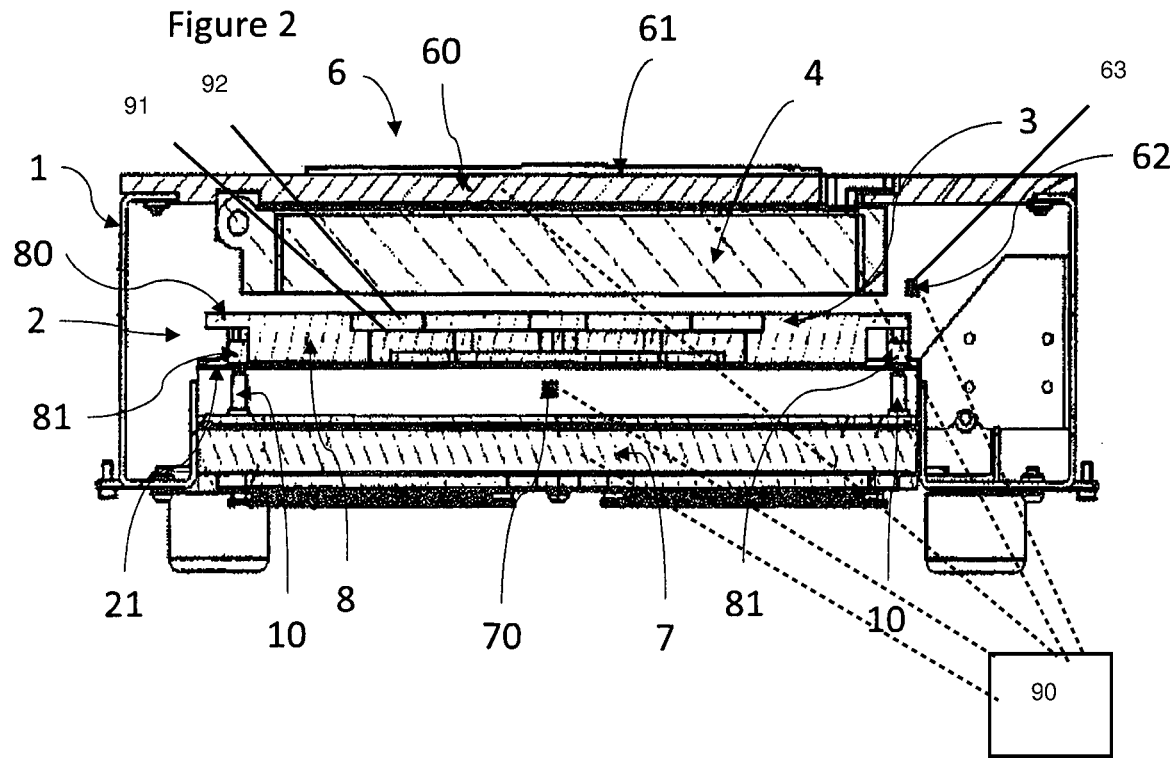
FIG. 2 shows a cross-sectional view along a vertical plane of the same detection device.

When referring to FIG. 2, we can see that the device according to the invention includes, inside the box 1, a detection surface 3 for receiving a receptacle closed by means of a transparent cover, which generally consists of a Petri box, and contains the growth medium for the microorganisms, such as a membrane or an agar medium.

The detection surface 3 of at least one receptacle 91 having a transparent cover 92 is associated with the drawer 2, so that the extraction (opened configuration) of drawer 2 permits the loading and unloading of the detection surface 3 or the corresponding receptacle.

The box 1 also contains a detection system 4, of the linear scanner type, movably mounted above the detection surface 3 when the drawer or tray 2 is closed, so as to be able to scan at least part of the detection surface 3, and preferably all of said surface 3.

The receptacle is held stationary on the detection surface 3 in order to permit the reading of the result.

Preferably, several receptacles are arranged on the detection surface 3 of the device 1, so as to permit a simultaneous detection of eventual contaminants in several different samples.

Thus, the receptacle(s) comprising a growth medium rest stationary on the detection surface 3, while the detection system 4 is movable in order to permit the detection of the formation of colonies on said growth media. This permits to prevent a movement of the media, which could lead to errors in the results being obtained.

The detection system 4 preferably includes at least one CCD (Charge-Coupled Device) sensor or CMOS (Complementary Metal Oxide Semiconductor) sensor.

The CCD or CMOS sensor advantageously has a resolution higher than or equal to 2400 dpi (dots per inch). Yet more preferably, the resolution is higher than or equal to 4800 dpi.

Such a resolution permits the detection through imaging of colonies present on the growth mediums, agar or membranes, positioned in the receptacles, when said colonies have a diameter smaller than or equal to 100 µm, even smaller than 50 µm, and yet more preferably smaller than or equal to 30 µm, through a useful magnification higher than or equal to 60.

The detection system 4 advantageously permits to take an image at regular time intervals.

The CCD or CMOS sensor of the detection system 4 is associated with an optical system comprised of at least one lighting and at least one optics, for example such as a lens. Preferably, the optical system also includes at least one mirror.

The incubation and detection device according to the invention comprises heating means 6 arranged in the upper portion of the box 1, above the detection surface 3, and which consist, non-restrictively, of an aluminum plate 60 associated with an electrical resistor 61. These heating means 6 are of course designed to maintain within the box 1 the desired incubation temperature.

The incubation and detection device according to the invention also comprises a system for preventing the formation of condensation. Indeed, as already mentioned above, the formation of condensation disturbs the reading of the surface of the agar or the membrane and does not permit to obtain satisfactory results.

It is therefore particularly important to solve this problem of formation of condensation that prevents a correct reading of the samples and can affect the accuracy of the results.

To this end, the system for preventing the formation of condensation includes cooling means 7 arranged in the lower portion of the box 1, under the drawer 2 or tray and therefore under the detection surface that carries the receptacles.

It should be noted that these cooling means 7 can preferably consist in Peltier-effect thermoelectric modules.

The system for preventing the condensation further includes a first temperature sensor 62, which is positioned above the receptacle or receptacles, and a second temperature sensor 70 arranged below the detection surface 3, and therefore below the receptacle or receptacles.

The system for preventing the condensation is complemented with management means or controller 90 being in communication with and collecting and analyzing the data or information collected by the first sensor 62 and the second sensor 70, and being in communication with and controlling the heating 6 and cooling 7 means in order to, on the one hand, generate the desired incubation temperature and, on the other hand, constantly apply a temperature gradient to the surface of the receptacle or receptacles.

A preferred means for measuring the temperature is obtained by using a thermocouple 63 permitting to measure in a contactless way the surface temperature of the receptacle.

The application of the temperature gradient will permit, in a particularly advantageous way, to avoid the formation of water droplets on the inner surface of the transparent cover of the receptacle. The reading of the growth of the colonies on the agar medium or the membrane will thus be facilitated.

In one advantageous embodiment, the temperature gradient applied by means of the system for preventing the condensation is at least 0.10° C.

This means that the temperature applied at the level of the cover of the receptacle, i.e. above said receptacle, is higher by at least 0.10° C. than the temperature, which is applied at the level of the bottom of the receptacle, i.e. below the latter.

Preferably, this gradient is between 0.10 and 1° C., and yet more preferably, this gradient is between 0.50 and 1° C.

Such a gradient is particularly optimal to prevent the formation of condensation on the cover of the receptacle.

When referring also to FIGS. 3a, 3b and 3c, there is a removable tray 8, which constitutes the detecting surface aimed at receiving the receptacles, not shown.

This removable tray 8 is designed removable with respect to the drawer 2. Thus, the tray 2 of the drawer includes a frame 21, partially visible in FIG. 2, on which the removable tray 8 can rest by its peripheral edge 80, or part thereof, when the drawer 2 is maintained extracted from the box 1.

The removable tray 8 also comprises, on the lower side and on the periphery, shims 81 aimed at cooperating with adjustable stops 10, of the type with a screw, for example, the box 1 includes below the space of evolution of the drawer 2.

In operation, during the closing of the drawer 2 or tray, the shims 81 rest against the adjustable stops 10, and remain there during the incubation and the detections, the removable tray 8 then being released from the drawer 2 or tray. The adjustment of the stops permits an accurate positioning of the removable tray 8, and therefore of the receptacles it carries, relative to the detection system 4, irrespective of the drawer 2.

In FIGS. 3a, 3b and 3c we can see that the removable tray 8 includes recesses 82, in this case twelve in number, each aimed at receiving a receptacle, not shown.

These recesses 82 each consist of a hollow accommodation permitting to wedge the receptacle.

When referring more particularly to FIG. 3c, we can see that depending on the position of the recess 82 on the removable tray 8, the bottom 83 of the recess 82 has a particular inclination relative to the general plane of the removable tray 8. Thus, the median recesses 82, relative to the XX' axis of movement of the detecting means relative to the removable tray 8, have a bottom 83 parallel to the general plane of the removable tray 8, while the side recesses 82 have a bottom 83 inclined towards the central line.

These configurations permit to avoid the optical aberrations likely to prevent or disturb a detection of the colonies.

Finally, it should be noted, as can be seen in FIG. 1, that the detection system 4, such as a scanner, of the incubation and detection device according to the invention includes a calibration system 9 having the particularity of being component extractable from the drawer 2 of the box 1, and preferably removable, for the purposes of cleaning and/or replacement.

The incubation and detection device according to the invention has the advantage, compared to those of the prior art, of a compactness and simplicity of manufacture.

It also provides the advantage of a possible modularity, since it can be dimensioned for processing a varying number of receptacles, by adjusting the removable tray 8 for example, but also because several boxes 1 can be stacked and/or juxtaposed, without therefore representing an important space.

These advantages are essentially due to the detection system being used as well as to how it is implemented. This detection system could however not be as performant without any, or all, of the various above-mentioned features.

We claim:

1. A device for incubation and fast detection without fluorescence measurement of colonies resulting from multiplication of microorganisms present in a sample to be tested, the device comprising:
   a box having a drawer with a front portion, said drawer having an opened configuration outside of said box and a closed configuration within said box;

heating means being above said drawer when said drawer is in said closed configuration;
a cooling means being below said drawer when said drawer is in said closed configuration;
at least one receptacle being comprised of a transparent cover so as to define a detection surface, said at least one receptacle being between said heating means and said cooling means when said drawer is in said closed configuration;
a detection system being comprised of an optical system so as to visualize through said transparent cover of said at least one receptacle;
a first temperature sensor above said at least one receptacle at said detection surface, below said detection system, and below said heating means;
a second temperature sensor below said at least one receptacle and above said cooling means; and
management means being connected to said first sensor, said second sensor, said heating means, and said cooling means so as to collect and analyze information collected by said first sensor and said second sensor, so as to control said heating means and said cooling means, so as to generate a desired incubation temperature, so as to permanently apply a temperature gradient at said detection surface of said at least one receptacle, and so as to prevent condensation as detection surface.

2. The device for incubation and fast detection, according to claim 1, wherein the detection system is further comprised of:
a linear scanner mounted movable and flat above said detection surface; and
at least one detecting sensor, said detecting sensor being selected from a group consisting of a CCD sensor and a CMOS sensor,
wherein said optical system is comprised of:
at least one light; and
at least one optic associated with said light.

3. The device for incubation and fast detection, according to claim 1, further comprising:
a removable tray slidable mounted within said tray portion of said drawer, said at least one receptacle being housed in said removable tray.

4. The device for incubation and fast detection, according to claim 3, wherein said removable tray is comprised of shims provided on a periphery of said removable tray and on an under side of said removable tray;
wherein said tray portion is comprised of stops, and
wherein said shims engage said stops so at to set a distance of said detection surface to said optical system of said detection system.

5. The device for incubation and fast detection, according to claim 4, wherein said detection surface is inclined relative to said optical system of said detection system.

6. The device for incubation and fast detection, according to claim 4, wherein said optical system is further comprised of a calibration system, said calibration system being removable from said box.

7. The device for incubation and fast detection, according to claim 1, wherein said first temperature sensor is comprised of a thermocouple.

* * * * *